US010023521B2

(12) United States Patent
Uhrich et al.

(10) Patent No.: US 10,023,521 B2
(45) Date of Patent: Jul. 17, 2018

(54) PROCESS AND INTERMEDIATES FOR PREPARING POLY(ANHYDRIDE-ESTERS)

(71) Applicant: Rutgers, the State University of New Jersey, New Brunswick, NJ (US)

(72) Inventors: Kathryn E. Uhrich, New Brunswick, NJ (US); Jonathan J. Faig, New Brunswick, NJ (US); Kervin Smith, New Brunswick, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/318,306

(22) PCT Filed: Jun. 10, 2015

(86) PCT No.: PCT/US2015/035143
§ 371 (c)(1),
(2) Date: Dec. 12, 2016

(87) PCT Pub. No.: WO2015/191742
PCT Pub. Date: Dec. 17, 2015

(65) Prior Publication Data
US 2017/0121267 A1    May 4, 2017

Related U.S. Application Data

(60) Provisional application No. 62/035,236, filed on Aug. 8, 2014, provisional application No. 62/011,917, filed on Jun. 13, 2014.

(51) Int. Cl.
C07C 69/76    (2006.01)
C07C 67/08    (2006.01)

(52) U.S. Cl.
CPC ................... C07C 67/08 (2013.01)

(58) Field of Classification Search
CPC ............ A61K 47/48192; A61K 31/765; C07C 67/08; B21B 1/16; C21D 8/06; C22C 38/00; C22C 38/28; C22C 38/50
See application file for complete search history.

(56) References Cited

U.S. PATENT DOCUMENTS

| | | |
|---|---|---|
| 2,607,799 A | 8/1952 | Weesner |
| 3,652,502 A | 3/1972 | Caldwell et al. |
| 3,933,747 A | 1/1976 | Nowak et al. |
| 4,062,855 A | 12/1977 | Allan et al. |
| 4,126,445 A | 11/1978 | Allan et al. |
| 4,164,560 A | 8/1979 | Folkman et al. |
| 4,298,595 A | 11/1981 | Parkinson et al. |
| 4,375,968 A | 3/1983 | Manhart et al. |
| 4,414,203 A | 11/1983 | Cabardo, Jr. et al. |
| 4,591,496 A | 5/1986 | Cohen et al. |
| 4,612,302 A | 9/1986 | Szabo et al. |
| 4,684,620 A | 8/1987 | Hruby et al. |
| 4,757,128 A | 7/1988 | Domb et al. |
| 4,789,724 A | 12/1988 | Domb et al. |
| 4,792,598 A | 12/1988 | Ziegast |
| 4,851,487 A | 7/1989 | Yaniger et al. |
| 4,853,371 A | 8/1989 | Coy et al. |
| 4,857,311 A | 8/1989 | Domb et al. |
| 4,868,274 A | 9/1989 | Gupta et al. |
| 4,886,870 A | 12/1989 | D'Amore et al. |
| 4,888,176 A | 12/1989 | Langer et al. |
| 4,891,225 A | 1/1990 | Langer et al. |
| 4,906,474 A | 3/1990 | Langer et al. |
| 4,916,204 A | 4/1990 | Domb et al. |
| 4,933,431 A | 6/1990 | Domb et al. |
| 4,938,949 A | 7/1990 | Borch et al. |
| 4,997,904 A | 3/1991 | Domb |
| 4,999,417 A | 3/1991 | Domb |
| 5,019,379 A | 5/1991 | Domb et al. |
| 5,032,216 A | 7/1991 | Felten |
| 5,082,925 A | 1/1992 | Shalaby et al. |
| 5,160,745 A | 11/1992 | Deluca et al. |
| 5,175,235 A | 12/1992 | Domb et al. |
| 5,235,030 A | 8/1993 | Koide |
| 5,259,968 A | 11/1993 | Emert et al. |
| 5,264,540 A | 11/1993 | Cooper et al. |
| 5,290,494 A | 3/1994 | Coombes et al. |
| 5,317,079 A | 5/1994 | Domb et al. |
| 5,364,725 A | 11/1994 | Wilson et al. |
| 5,498,729 A | 3/1996 | Domb |
| 5,512,131 A | 4/1996 | Kumar et al. |
| 5,514,764 A | 5/1996 | Frechet et al. |
| 5,518,730 A | 5/1996 | Fuisz |
| 5,545,409 A | 8/1996 | Laurencin et al. |
| 5,629,009 A | 5/1997 | Laurencin et al. |
| 5,660,851 A | 8/1997 | Domb |
| 5,721,131 A | 2/1998 | Rudolph et al. |
| 5,776,748 A | 7/1998 | Singhvi et al. |
| 5,798,115 A | 8/1998 | Santerre et al. |
| 5,837,278 A | 11/1998 | Geistlich et al. |
| 5,889,028 A | 3/1999 | Sandborn et al. |
| 5,891,477 A | 4/1999 | Lanza et al. |
| 5,902,110 A | 5/1999 | Alfano et al. |
| 5,902,599 A | 5/1999 | Anseth et al. |

(Continued)

FOREIGN PATENT DOCUMENTS

| | | |
|---|---|---|
| AU | 750424 | 3/2003 |
| CA | 2393676 | 7/2002 |

(Continued)

OTHER PUBLICATIONS

Prudencio et al. (Macromolecules, vol. 38, No. 16, p. 6895-6901, published 2005).*

(Continued)

Primary Examiner — Yevgeny Valenrod
Assistant Examiner — Blaine G Doletski
(74) Attorney, Agent, or Firm — Viksnins Harris Padys Malen LLP

(57) ABSTRACT

Certain embodiments of the invention provide a method comprising treating a hydroxy-carboxylic acid compound with a compound of formula (I) in the absence of a solvent, to provide a diacid of formula (II), wherein R is a linker molecule; wherein each Y is independently a leaving group; and wherein X is a residue of a biologically active compound.

20 Claims, 4 Drawing Sheets

(56) References Cited

U.S. PATENT DOCUMENTS

| | | |
|---|---|---|
| 5,916,585 A | 6/1999 | Cook et al. |
| 5,937,758 A | 8/1999 | Maracas et al. |
| 5,942,252 A | 8/1999 | Tice et al. |
| 5,958,911 A | 9/1999 | Evans et al. |
| 5,969,020 A | 10/1999 | Shalaby et al. |
| 6,071,530 A | 6/2000 | Polson et al. |
| 6,123,956 A | 9/2000 | Baker et al. |
| 6,153,212 A | 11/2000 | Mao et al. |
| 6,171,610 B1 | 1/2001 | Vacanti et al. |
| 6,280,772 B1 | 8/2001 | Pinkus |
| 6,365,149 B2 | 4/2002 | Vyakarnam et al. |
| 6,468,519 B1 | 10/2002 | Uhrich |
| 6,486,214 B1 | 11/2002 | Uhrich |
| 6,602,915 B2 | 8/2003 | Uhrich |
| 6,613,807 B2 | 9/2003 | Uhrich |
| 6,685,928 B2 | 2/2004 | Uhrich et al. |
| 6,689,350 B2 | 2/2004 | Uhrich |
| 7,122,615 B1 | 10/2006 | Uhrich |
| 7,396,527 B2 | 7/2008 | Uhrich |
| 7,411,031 B2 | 8/2008 | Uhrich et al. |
| 7,534,852 B2 | 5/2009 | Uhrich |
| 7,662,864 B2 | 2/2010 | Kanamathareddy et al. |
| 7,666,398 B2 | 2/2010 | Uhrich |
| 7,985,415 B2 | 7/2011 | Giroux |
| 8,017,714 B2 | 9/2011 | Uhrich |
| 8,088,405 B2 | 1/2012 | Uhrich et al. |
| 8,221,790 B2 | 7/2012 | Uhrich |
| 8,232,322 B2 | 7/2012 | East et al. |
| 8,241,668 B2 | 8/2012 | Uhrich et al. |
| 8,263,060 B2 | 9/2012 | Uhrich et al. |
| 8,361,453 B2 | 1/2013 | Uhrich et al. |
| 8,741,317 B2 | 6/2014 | Uhrich et al. |
| 8,747,832 B2 | 6/2014 | Uhrich et al. |
| 9,108,070 B2 | 8/2015 | Kanamathareddy et al. |
| 9,144,579 B2 | 9/2015 | Uhrich et al. |
| 9,387,250 B2 | 7/2016 | Uhrich et al. |
| 2003/0035787 A1 | 2/2003 | Uhrich et al. |
| 2003/0059469 A1 | 3/2003 | Uhrich et al. |
| 2003/0086895 A1 | 5/2003 | Hanes et al. |
| 2004/0038948 A1 | 2/2004 | Uhrich et al. |
| 2004/0044125 A1 | 3/2004 | Uhrich et al. |
| 2004/0096476 A1 | 5/2004 | Uhrich et al. |
| 2004/0198641 A1 | 10/2004 | Uhrich et al. |
| 2004/0228832 A1 | 11/2004 | Uhrich et al. |
| 2005/0031577 A1 | 2/2005 | Uhrich et al. |
| 2005/0048121 A1 | 3/2005 | East et al. |
| 2005/0053577 A1 | 3/2005 | Uhrich et al. |
| 2005/0089504 A1 | 4/2005 | Uhrich et al. |
| 2005/0089506 A1 | 4/2005 | Uhrich et al. |
| 2005/0100526 A1 | 5/2005 | Uhrich et al. |
| 2005/0131199 A1 | 6/2005 | Uhrich et al. |
| 2005/0249697 A1 | 11/2005 | Uhrich et al. |
| 2006/0013851 A1 | 1/2006 | Giroux et al. |
| 2006/0039964 A1 | 2/2006 | Uhrich et al. |
| 2006/0057179 A1 | 3/2006 | Giroux et al. |
| 2007/0098800 A1 | 5/2007 | Giroux et al. |
| 2007/0196417 A1 | 8/2007 | Uhrich et al. |
| 2008/0234235 A1 | 9/2008 | Uhrich et al. |
| 2010/0152410 A1 | 6/2010 | East et al. |
| 2010/0291180 A1 | 11/2010 | Uhrich et al. |
| 2010/0291181 A1 | 11/2010 | Uhrich et al. |
| 2010/0310498 A1 | 12/2010 | Kanamathareddy et al. |
| 2011/0022161 A1 | 1/2011 | Uhrich et al. |
| 2013/0022569 A1 | 1/2013 | Uhrich et al. |
| 2013/0071458 A1 | 3/2013 | Kanamathareddy et al. |
| 2014/0030341 A1 | 1/2014 | Uhrich et al. |
| 2014/0050692 A1 | 2/2014 | Uhrich et al. |
| 2014/0120057 A1 | 5/2014 | Uhrich et al. |
| 2016/0058776 A1 | 3/2016 | Kanamathareddy et al. |
| 2016/0130211 A1 | 5/2016 | Uhrich et al. |
| 2016/0175343 A1 | 6/2016 | Uhrich et al. |

FOREIGN PATENT DOCUMENTS

| | | |
|---|---|---|
| DE | 288311 | 3/1991 |
| DE | 0288387 | 3/1991 |
| EP | 0246341 | 11/1987 |
| EP | 0463932 | 1/1992 |
| EP | 0483429 | 5/1992 |
| EP | 0498283 | 8/1992 |
| EP | 0580386 | 1/1994 |
| EP | 0511292 | 4/2000 |
| GB | 2226821 | 7/1990 |
| JP | 51134729 | 11/1976 |
| JP | 53082743 | 7/1978 |
| JP | 56007716 | 1/1981 |
| JP | 6255797 | 12/1985 |
| JP | 61186309 | 8/1986 |
| JP | 06328857 | 11/1994 |
| JP | 07149044 | 6/1995 |
| NL | 9000237 | 8/1991 |
| WO | 1989001005 | 2/1989 |
| WO | 199009779 | 9/1990 |
| WO | 199109831 | 7/1991 |
| WO | 199118940 | 12/1991 |
| WO | 199739738 | 10/1997 |
| WO | 199744016 | 11/1997 |
| WO | 199749385 | 12/1997 |
| WO | 199836013 | 8/1998 |
| WO | 1999012990 | 3/1999 |
| WO | 199929885 | 6/1999 |
| WO | 199936107 | 7/1999 |
| WO | 200066730 | 11/2000 |
| WO | 2001028492 | 4/2001 |
| WO | 2001041753 | 6/2001 |
| WO | 2002009767 | 2/2002 |
| WO | 2002009768 | 2/2002 |
| WO | 2002009769 | 2/2002 |
| WO | 2003046034 | 6/2003 |
| WO | 2003065928 | 8/2003 |
| WO | 2003066053 | 8/2003 |
| WO | 2003072020 | 9/2003 |
| WO | 2004006863 | 1/2004 |
| WO | 2004039355 | 5/2004 |
| WO | 2004045549 | 6/2004 |
| WO | 2005039489 | 5/2005 |
| WO | 2005042600 | 5/2005 |
| WO | 2006127667 | 11/2006 |
| WO | 2007143698 | 12/2007 |
| WO | 2008034019 | 3/2008 |
| WO | 2008103744 | 8/2008 |
| WO | 2008128193 | 10/2008 |
| WO | 2009026544 | 2/2009 |
| WO | 2011098839 A2 | 8/2011 |
| WO | 2012139015 | 10/2012 |
| WO | 2014194055 | 12/2014 |
| WO | 2016164898 A1 | 10/2016 |

OTHER PUBLICATIONS

Chandorkar et al. (Cross-Linked, Biodegradable, Cytocompatible Salicylic Acid Based Polyesters for Localized, Sustained Delivery of Salicylic Acid: An In Vitro Study, Biomacromolecules ACS, 15, p. 863-875, published Feb. 11, 2014).*

Uhrich, "Degradation of poly(anhydride-co-imides): Novel Polymers for Orthopedic Applications", Mat. Res. Soc. Symp. Proc., 394, 41-46, (1995).

Uhrich, "In Vitro Degradation Characteristics of Poly(anhydride-imides) Containing Pyromellitylimidoalanine", J. Appl. Polymer Sci., Part A, Polym. Chem., 34(7), 1261-1269, (1996).

Uhrich, "In Vitro Degradation Characteristics of Poly(anhydride-imides) Containing trimellitylimidoglycine", J. Appl. Polymer. Sci., 63(11), 1401-1411, (1997).

Uhrich, "Poly(anhydride-ester) Degradation: Mechanical Changes and Correlation to Antibiotic Release", American Chemical Society, Abstracts of Papers, Part 2, Abstract No. 121, 221st ACS National Meeting, San Diego, CA, Abstract 121, (2001).

Uhrich, et al., "Polymeric systems for controlled drug release", Chem Rev 99 (11), 3181-3198 (1999).

(56) References Cited

OTHER PUBLICATIONS

Uhrich, "Synthesis and Characterization of Degradable poly(anhydride-co-imides)", Macromolecules, 28(7), 2184-2193, (1995).
Uhrich, "Synthesis of Aminosalicylate-based polyanhydride Prodrugs: Esters, Amides, and Azos", American Chemical Society, Abstracts of Papers, Part 2, Abstract No. 407, 222nd ACS National Meeting, Chicago, IL, Abstract 407, (2001).
Woo, "Biological Characterization of a Novel Biodegradable Antimicrobial Polymer Synthesized with Fluoroquinolones", J. Biomed. Mater. Res. 59, 35-45, (2002).
Woo, et al., "Synthesis and characterization of a novel biodegradable antimicrobial polymer", Biomaterials, 21, 1235-1246 (2000).
Yazdi, et al., "Effects of non-steroidal anti-inflammatory drugs on demineralized bone-induced bone formation", Journal of Periodontal Research, 27(1), 28-33, (Jan. 1992).
Yoda, "Synthesis of polyanhydrides. XII. Crystalline and high melting polyamidepolyanhydride of methylenebis(p-carboxybhenyl)amide", Journal of Polymer Science, 1, 1323-1338, (1963).
Aebischer, et al., "Basic fibroblast growth factor released from synthetic guidance channels facilitates peripheral nerve regeneration across long nerve gaps", Journal of Neuroscience Research, 23(3), 282-289, (Jul. 1989).
Allinger, et al., "Organic Chemistry", Worth Publishers, Inc., p. 528 (1971).
Anastasiou, "Novel Polyanhydrides with Enhanced Thermal and Solubility Properties", Macromolecules, 33(17), 6217-6221, (2000).
Branch, "Microstamp patterns of biomolecules for high resolution neuronal networks", Medical & Biological Engineering & Computing, 36(1), 135-41, (Jan. 1998).
Brown, "A Polymeric Drug for Treatment of Inflammatory Bowel Disease", Journal of Medicinal Chemistry, 26(9), 1300-1307, (1983).
Brown, et al., "Transdermal delivery of drugs", Annual Review of Medicine, 39, 221-9, (1988).
Campo, "Polyanhydrides: the effects of ring substitution changes on polymer properties", Polymer Bulletin, 42, 61-68, (1999).
Capello, et al., "What is a green solvent? A comprehensive framework for the environmental assessment of solvents", Green Chemistry 9, 927-934 (2007).
Carbone, et al., "Design and Synthesis of Fast-Degrading Poly(anhydride-esters)", Macromol. Rapid Commun., 30, 1021-1026 (2009).
Chafi, "Dosage Form with Salicylic Acid Attached to the Polyanhydride Polymer Dispersed in an Eudragit Matrix", International Journal of Pharmaceutics, 52, 203-211, (1989).
Chatterjee, et al., "Mechanism for the Increase in Solubility of Deoxyhemoglobin S due to Cross-Linking the Beta Chains Between Lysine-82 Beta1 and Lysine-82 Beta 2", Biochemistry, 21, 5901-5909, (1982).
Chen, "Effect of protein and cell behavior on pattern-grafted thermoresponsive polymer", Journal of Biomedical Materials Research, 42(1), 38-44, (Oct. 1998).
Conix, "Aromatic Polyanhydrides, a New Class of High Melting Fiber-Forming Polymers", Journal of Polymers Science, XXIX, 343-353, (1958).
Conix, "New High-Melting Fibre-Forming Polymers", Die Makromolekulare Chemie, XXIV, 76-78, (1957).
Anastasiou, "Novel, Degradable Polyanhydrides", 25th Annual Meeting Transactions of the Society for Biomaterials, Abstract, 79, (1999).
Anastasiou, "Synthesis of Novel, Degradable Polyanhydrides Containing Para-Aminosalicylic Acid as Drug Delivery Devices for Tuberculosis Treatment", Polymer Preprints, 41(2), 1366-1367, (Aug. 2000).
Attawia, "Biocompatibility Testing of Poly(anhydride-co-imides) Containing Pyromellitylimidoalanine", The 21st Annual Meeting of the Society for Biomaterials, Abstract, 222, (Apr. 5-9, 1994).

Attawia, "Cytotoxicity testing ofpoly(anhydride-co-imides) for orthopedic applications", Journal of Biomedical Materials Research, 29(10), 1233-1240, (1995).
Attawia, "In vitro bone biocompatibility of poly(anhydride-co-imides) containing pyromellitylimidoalanine", Journal of Orthopedic Research, 14(3), 445-454, (1996).
Attawia, "Proliferation, Morphology, and Protein Expression by Osteoblasts Cultured on Poly(anhydride-co-amides)", Journal of Biomedical Materials Research, 48(3), 322-327, (1999).
Attawia, "Regional drug delivery with radiation for the treatment of Ewing's sarcoma—in vitro development of a taxol release system", Journal of Controlled Release, 71, 193-202 (2001).
Attawia, "The Long Term Osteoblast Response to Poly(anhydride-co-imides): A New Degradable Polymer for Use in Bone", Proceedings of the Fifth World Biomaterials Congress, Toronto, Canada, 113, (1996).
Beaton, "Synthesis of a novel poly(anhydride-ester)", The Rutgers Scholar—An Electronic Bulletin of Undergraduate Research, 3, 1-7, (2001), http://www.scils.rutgers.edu/~weyang/ejournal/volume03/beatuhri/beatuhri.htm.
Bedell, "Processing and Hydrolytic Degradation of Aromatic, Ortho-Substituted Polyanhydrides", Journal of Applied Polymer Science, 80, 32-38, (2001).
Brambley, et al., "Microlithography: an overview", Advanced Materials for Optics and Electronics, 4(2), 55-74, (Mar.-Apr. 1994).
Domb, "Polyanhydrides. I. Preparation of High Molecular Weight Polyanhydrides", Journal of Polymer Science: Part A: Polymer Chemistry, 25, 3373-3386, (1987).
Domb, "Synthesis and Characterization of Biodegradable Aromatic Anhydride Copolymers", Macromolecules, 25, 12-17, (1992).
Dontha, "Generation of biotin/avidin/enzyme nanostructures with maskless photolithography", Analytical Chemistry, 69(14), 2619-25, (Jul. 15, 1997).
Dube, et al., "Applying the Principles of Green Chemistry to Polymer Production Technology", Macromolecular Reaction Engineering 8(1), 7-28 (2014).
Dukovic, "Novel degradable poly(anhydride-esters) for controlled drug release", The Rutgers Scholar—An Electronic Bulletin of Undergraduate Research, 1, 1-10, (1999), http://www.scils.rutgers.edu/~weyang/ejournal/volume01/uhriduko/uhriduko.htm.
Erdman, et al., "Synthesis and Characterization of a Polymeric Prodrug", Proceedings of the American Chemical Society Division of Polymeric Materials: Science and Engineering, 78, Abstract Spring Meeting, Dallas, TX, pp. 194, (Apr. 1998).
Erdmann, et al., "Chapter 5, Polymeric Prodrugs: Novel Polymers with Bioactive Components in Tailored Polymeric Materials for Controlled Delivery Systems", ACS Symposium Series 709, Developed from a symposium sponsored by the Division of Polymer Chemistry at the 214th National Meeting of the American Chemical Society, Washington D.C., 83-91 (1998).
Erdmann, "Degradable poly(anhydride ester) implants: effects of localized salicylic acid release on bone", Biomaterials, 21(24), 2507-2512, (2000).
Erdmann, "Polymer Prodrugs with Pharmaceutically Active Degradation Products", Polymer Preprints, 38(2), 570-571, (1997).
Erdmann, "Polymeric Prodrugs: Novel Polymers for Delivery of Salicylic Acid", Annals of Biomedical Engineering, 26 (Suppl. 1), Abstract No. PB.26, Annual Fall Meeting, S-124, (1998).
Erdmann, "Polymeric Salicylic Acid: In Vitro and In Vivo Degradation", Polymer Preprints, 39(2), 224-225, (1998).
Conix, "Poly [1,3-bis (p carboxyphenoxy)—Propane anhydride]", Macromolecular Synthesis, 2, 95-99, (1996).
Cotlier, "Distribution of salicylate in lens and intraocular fluids and its effect on cataract formation", American Journal of Medicine, 74 (6A), 83-90 (1983).
Cotlier, "Senile Cataracts: Evidence for Acceleration by Diabetes and Deceleration by Salicytate", Canadian Journal of Ophthalmology, 16(3), 113-118 (1981).
Davaran, "Release of 5-amino Salicylic Acid from Acrylic Type Polymeric Prodrugs Designed for Colon-specific Drug Delivery", Journal of Controlled Release, 58(3), 279-287, (1999).

(56) References Cited

OTHER PUBLICATIONS

Davies, "The Analysis of the Surface Chemical Structure of Biomedical Aliphatic Polyanhydrides Using SPX and ToF-SIMS", Journal of Applied Polymer Science, 42, No. 6, New York, US, 1597-1605, (Mar. 20, 1991).
Delamarche, et al., "Patterned delivery of immunoglobulins to surfaces using microfluidic networks", Science, 276 (5313), 779-781, (May 2, 1997).
Dewez, et al., "Adhesion of mammalian cells to polymer surfaces: from physical chemistry of surfaces to selective adhesion on defined patterns", Biomaterials, 19(16), 1441-1445, (Aug. 1998).
Domb, et al., "Biodegradable polymers derived from amino acids", Biomaterials, vol. 11, pp. 686-689, 1990.
Domb, et al., "Biodegradable Polymers Derived from Amino Acids", Polymer Preprints, Division of Polymer Chemistry ACS 30(2), 189-190 (1989).
Domb, et al., "Excretion of a radiolabelled anticancer biodegradable polymeric implant from the rabbit brain", Biomaterials 16, 1069-1072 (1995).
Domb, et al., "Poly(anhydrides). 2. One-Step Polymerization using Phosgene or Diphosgene as Coupling Agents", Macromolecules 21, 1925-1929 (1988).
Fessenden, et al., "Organic Chemistry", PWS Publishers, Second Edition, p. 617 (1982).
Giammona, "Polymeric Prodrugs alpha beta poly-hyroxyethyl-dl-aspartamide as macromolecular carrier for some non-steroidal anti-inflammatory agents", Abstracts from Database BIOSIS Online, Biosciences Information Service, Philadelphia, PA, Original Publication from the International Journal of Pharmaceutics (Amsterdam), 1 page (1989).
Giammona, "Polymeric Prodrugs Alpha Beta Poly-N-hydroxyethyl-DL-aspartamide as a Macromolecular Carrier for Some Non-Steroidal Anti-inflammatory Agents", International Journal of Pharmaceutics, 57, 55-62, (1989).
Gouin, et al., "New Polyanhydrides Made from a Bile Acid Dimer and Sebacic Acid: Synthesis, Characterization and Degradation", Macromolecules, 33, 5379-5383, (2000).
Herbert, "Micropatterning gradients and controlling surface densities of photoactivatable biomolecules on self-assembled monolayers of oligo(ethylene glycol) alkanethiolates", Chemistry & Biology, 4(10), 731-7, (Oct. 1997).
Ibim, "Controlled Release Based on Poly(anhydride-co-imides)", Proc. Intern. Symp. Control. Rel. Bioact. Mater., 22, 2 pgs, (1995).
Ibim, "Poly(anhydride-co-imides): In Vivo Biocompatibility in a rat model", Biomaterials, 19(10), 941-951, (1998).
Ibim, "Preliminary in vivo report on the osteocompatibility of poly(anhydride-co-imides) evaluated in a tibial model.", Journal of Biomedical Material Research, 43(4), 374-379, (Winter 1998).
Ito, "Micropatterned immobilization of epidermal growth factor to regulate cell function", Bioconjugate Chemistry, 9(2), 277-82, (Mar.-Apr. 1998).
James, "Patterned Protein Layers on Solid Substrates by Thin Stamp Microcontact Printing", Langmuir, 14(4), 741-744, (1998).
Jeffcoat, "The Effect of Systemic Flurbiprofen on Bone Supporting Dental Implants", Journal of American Dental Associate, 126, 305-311 (1995).
Jiang, "Synthesis, Characterization and In Vitro Degradation of a New Family of Alternate Poly(ester-anhydrides) Based on Aliphatic and Aromatic Diacids", Biomaterials, 22(3), 211-218, (2001).
Jucker, et al., "Fetal rat septals cells adhere to and extend processes on basement membrane, laminin, and a synthetic peptide from the laminin A chain sequence", Journal of Neuroscience Research, 28(4), 507-17, (Apr. 1991).
Kleinfeld, "Controlled outgrowth of dissociated neurons on patterned substrates", Journal of Neuroscience, 8(11), 4098-120, (Nov. 1998).
Kricheldorf, et al., "Polyanhydrides, XI. Poly(ester-anhydride)s Derived from 4-Hydroxybenzoic Acid, Vanillic Acid, and Aliphatic Dicarboxylic Acids", J.M.S.—Pure Appl. Chem, A35(2), 359-373 (1998).
Krogh-Jespersen, "Synthesis of a Novel Aromatic Polyanhydride Containing Aminosalicylic Acid", Polymer Preprints, 41(1), 1048-1049, (2000).
Kumar, et al., "Polyanhydrides: an overview", Advanced Drug Delivery Reviews, 54, pp. 889-910, 2002.
Langer, "New Methods of Drug Delivery", Science, 249(4976), 1527-1533, (Sep. 1990).
Laurencin, "Poly(anhydrides-co-imides): In Vivo Biocompatibility Study", 23rd Annual Meeting of the Society for Biomaterials, New Orleans, LA, 483, (1997).
Laurencin, "The Biocompatibility of Poly(anhydride-co-imides): High Strength Polymers for Controlled Drug Delivery", Proc. 24th Int'l Symp. Control. Rel. Bioact. Mater., 973-974, (1997).
Laurencin, "The Bone Biocompatibility of Poly(anhydride-co-imides)—A new generation degradable Polymer for Orthopedic Applications", 41st Annual Meeting of the Orthopedic Research Society, Orlando, FL, 143-24, (1995).
Laurencin, et al., "The controlled delivery of radiosensitizers: taxol treatment for Ewing Sarcoma", Proceedings of the 25th Int'l Symp. Control. Rel. Bioact. Mater., pp. 236-237, (1998).
Leong, et al., "Synthesis of Polyanhydrides: Melt-Polycondensation, Dehydrochlorination and Dehydrate Coupling", Macromolecules 20, 705-712 (1987).
Longer, "Sustained-Release Drug Delivery Systems", Remington's Pharmaceutical Sciences, 18th Edition, Chapter 91, 1676-1693, (1990).
Macedo, et al., "The in vivo Response to a Bioactive Biodegradable Polymer", Journal of Dental Research, 78, Abstract No. 2827, 459, (1999).
Macedo, "The In Vivo Response to Bioactive Polyanhydride Monofilament", Journal of Dental Research, 79 (Abstract No. 3872), 627, (2000).
March, Advanced organic chemistry: reactions, mechanisms, and structure, 4th Edition, New York: Willey, 419-437 (1992).
Patent Cooperation Treaty, International Searching Authority, Search Report and Written Opinion for PCT/US15/35143, 10 pages, dated Sep. 3, 2015.
Pinther, "Synthesis of Polyanhydrides Containing Ester Groups", Die Makromolekulare Chemie, Rapid Communications, 11(8), 403-408, (Aug. 1990).
Prudencio, et al., "Effect of Linker Structure on Salicylic Acid-Derived Poly(anhydride-esters)", Macromolecules 38, 6895-6901 (2005).
Reynolds, et al., "Non-steroidal anti-inflammatory drug (NSAID)-derived poly(anhydride-esters) in bone and periodontal regeneration", Current Drug Delivery, 4(3), 233-239 (Jan. 1, 2007).
Schacht, "Polymers for Colon Specific Drug Delivery", Journal of Controlled Release, 39, 327-338, (1996).
Schmalenberg, "Microlithographic patterning of polymer substrates for directed neuronal", Polymeric Materials Science Engineering, 81, Fall Meeting, Aug. 22-26, 1999, New Orleans, LA., 97, (1999).
Schmalenberg, "Patterned Polymer Substrates for directing Neuronal Growth", ACS Regional Mid-Atlantic Research Meeting, (1999).
Schmalenberg, "Patterning of polymer substrates for directed neuronal growth studies", Laboratory for Surface Modification,(Mar. 18, 1999).
Schmalenberg, "Thin Stamp Microcontact Patterned Printing of Protein Layers on Polymer Substrates", Transactions: Twenty-Fifth Annual Meeting of the Society for Biomaterials, Apr. 28-May 2, (1999).
Schmeltzer, et al., "Comparison of salicylate-based poly(anhydride-esters) formed via melt-condensation versus solution polymerization", Journal of Biomaterials Science: Polymer Edition 19 (10), 1295-1306 (2008).
Schmeltzer, et al., "Optimized Synthesis of Salicylate-based Poly(anhydride-esters)", Polymer Bulletin 49 (6), 441-448 (2003).
Schroder, et al., "Towards sustainable polymer chemistry with homogeneous metal-based catalysts", Green Chemistry 16, 1637-1651 (2014).
Seidel, "Erosion of Poly(anhydride-co-imides): A Preliminary Mechanistic Study", J. Appl. Polym. Sci., 62(8), 1277-1283, (1996).

(56) References Cited

OTHER PUBLICATIONS

Senaratina, et al., "Acetyl salicylic acid (Aspirin) and salicylic acid induce multiple stress tolerance in bean and tomato plants", Plant Growth Regulation 30, 157-161 (2000).
Shen, "Morphological Characterization of Erodible Polymer Carriers for Drug Release", Proc. 26th Int'l Symp. Control. Rel. Bioact. Mater., 717-718, (1999).
Smith, et al., "Synthesis of Salicylic Acid based(poly anhydride) esters via Green Chemistry Methods", (poster) Celebration of Undergraduate Achievement, Department of Chemistry and Chemical Biology, Rutgers University; May 2014.
Spargo, et al., "Spatially controlled adhesion, spreading, and differentiation of endothelial cells on self-assembled molecular monolayers", Proceedings of the National Academy of Science USA,91(23), 11070-11074, (Nov. 8, 1994).
St. John, "Diffraction-based cell detection using a microcontact printed antibody grating", Analytical Chemistry, 70(6), 1108-11, (Mar. 15, 1998).
Stolle, et al., "Ball milling in organic synthesis: solutions and challenges", Chem Soc Rev 40, 2317-2329 (2011).
Swinyard, "Pharmaceutical Necessities", In: Remington's pharmaceutical sciences by Joseph P. Remington; Alfonso R. Gennaro, Easton, PA.: Mack Pub. Co.: ISBN: 0912734043, 1286-1329 (1990).
Tashiro, et al., "A synthetic peptide containing the IKVAV sequence from the A chain of laminin mediates cell attachment, migration, and neurite outgrowth", Journal of Biological Chemistry, 264(27), 16174-82, (Sep. 25, 1989).
Uhrich, "Chemical Changes during in vivo degradation of poly(anhydride-imide) matrices", Biomaterials, 19(22), 2045-2050, (1998).
Uhrich, "Synthesis and Characterization of poly(anhydride co-imides): Solution Polycondensation of Biodegradable Polymers Derived from Amino Acids", Proc. of the American Chemical Society, Division of Polymeric Materials: Science and Engineering, 70, Spring Meeting, San Diego, CA, 239-240, (1994).
Erdmann, et al., "Synthesis and degradation characteristics of salicylic acid-derived poly(anhydride-esters)", Biomaterials, 21(19), 1941-1946, (2000).
Faig, et al., "Exploring green methods through a one-pot salicylic acid-based poly(anhydride-ester) synthesis", Abstract No. 489, 248th ACS National Meeting & Exposition, San Francisco, California, 1 page, (Jun. 16, 2014).
Faig, et al., "Exploring green methods through a one-pot salicylic acid-based poly(anhydride-ester) synthesis", Poster, 248th ACS National Meeting & Exposition, San Francisco, California, 6 pages, (Aug. 12, 2014).
Zaugg, et al., "Modification of Hemoglobin with Analogs of Aspirin", The Journal of Biological Chemistry, 255(7), 2816-2821, (1980).

\* cited by examiner

PROCESS AND INTERMEDIATES FOR PREPARING POLY(ANHYDRIDE-ESTERS)

CROSS-REFERENCE TO RELATED APPLICATION(S)

This application claims priority from U.S. Provisional Application No. 62/011,917, filed Jun. 13, 2014 and from U.S. Provisional Application No. 62/035,236, filed Aug. 8, 2014, which applications are herein incorporated by reference.

BACKGROUND OF THE INVENTION

Green chemistry aims to mitigate the environmental, health, and economic concerns associated with traditional chemical processes by increasing reaction efficiencies, reducing waste, using innocuous materials, and developing biodegradable products. Poly(anhydride-esters) (PAEs) are biodegradable surface-eroding polymers that represent such biodegradable products, exhibiting a controlled, near zero-order release of naturally occurring bioactives. Current synthesis of bioactive-based PAEs use excessive solvents, hazardous purification chemicals, and multistep reactions. Therefore, improved and/or less-toxic methodologies for preparing PAEs are needed, as well as intermediates that are useful in the preparation of such polymers.

SUMMARY OF THE INVENTION

Accordingly, described herein are synthetic methodologies that implement principles of green chemistry. For example, certain embodiments of the invention provide a method comprising treating a hydroxy-carboxylic acid compound:

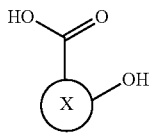

with a compound of formula (I):

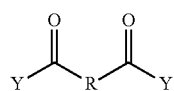

in the absence of a solvent, to provide a diacid of formula (II):

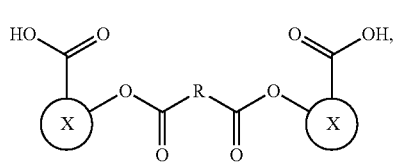

wherein R is a linker molecule; each Y is independently a leaving group; and wherein
X is a residue of a biologically active compound.

DETAILED DESCRIPTION

Figure 1:
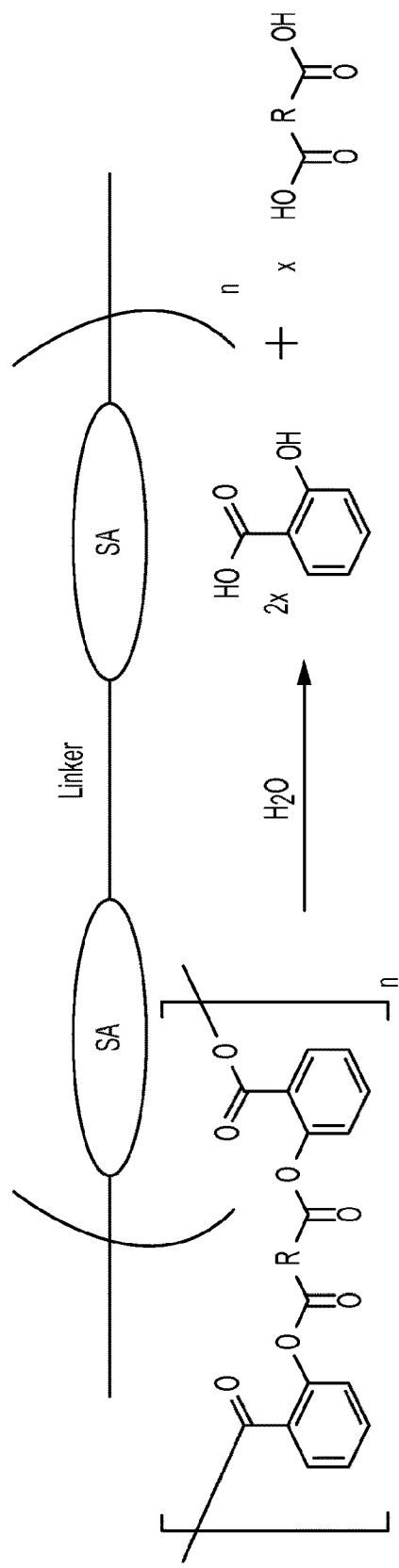
FIG. 1. Scheme illustrating biodegradation of SA-based PAEs; each unit is composed of two salicylic acid moieties connected by a linker molecule.

As described herein, synthetic methods that implement the principles of green chemistry have been established for the generation of PAEs. Examples of such methods are presented in Examples 1 and 2, which describe the synthesis of SA-PAEs using a one-pot methodology. Specifically, using a stoichiometric amount of pyridine, two moieties of salicylic acid (SA) were chemically conjugated through adipoyl chloride under solvent-free conditions to acquire SA diacid. SA diacid was subsequently activated and polymerized under high vacuum and heat to generate SA-based poly(anhydride-esters) via a one-pot reaction. This one-pot reaction methodology greatly reduced reaction time (i.e., twice as fast) while increasing efficiency (i.e., higher molecular weight Mw). Additionally, polymers were characterized to ensure that the greener methodology did not detrimentally impact physicochemical and thermal properties. This one-pot methodology offers a means for synthesizing poly(anhydride-esters) for various biomedical applications while overcoming traditional polymer synthesis limitations such as toxic solvent entrapment and long reaction time from starting material to polymer product. While these Examples describe the generation of SA-PAEs, this methodology may be applied to the synthesis of PAEs comprising other compounds, e.g., other hydroxy-carboxylic acid compounds.

Accordingly, certain embodiments of the invention provide a method comprising treating a hydroxy-carboxylic acid compound:

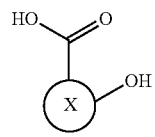

with a compound of formula (I):

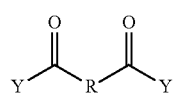

in the absence of a solvent, to provide a diacid of formula (II):

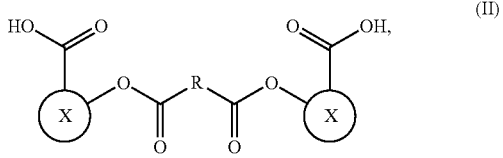

wherein R is a linker molecule; wherein each Y is independently a leaving group; and wherein X is a residue of a hydroxy-carboxylic acid compound.

It should be understood that in formula II, when X is the "residue of a hydroxy-carboxylic acid compound" X represents the structure of the compound other than the oxy group (—O—) and the carboxy group (—COOH) shown attached to X in formula (II). Hydroxy-carboxylic acid compounds that may be used in the methods described herein generally have a relatively low molecular weight of approximately 1,000 daltons or less (e.g., about 900 daltons, 800 daltons, 700 daltons, 600 daltons, 500 daltons, 400 daltons, 300 daltons, 200 daltons, 100 daltons, 50 daltons, etc.). Additionally, while these compounds must contain within their molecular structure at least one carboxylic acid group and one hydroxy group, the compound may also comprise other functional groups.

Certain other embodiments of the invention provide a method comprising treating a hydroxy-carboxylic acid compound:

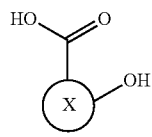

with a compound of formula (I):

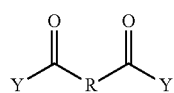

in the absence of a solvent, to provide a diacid of formula (II):

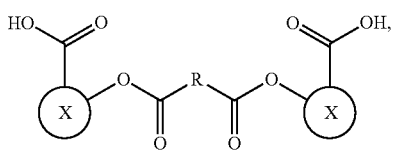

wherein R is a linker molecule; wherein each Y is independently a leaving group; and wherein X is a residue of a biologically active compound.

In certain embodiments, the method further comprises treating the diacid of formula (II) with an acid anhydride (e.g., acetic anhydride) and heat to provide the corresponding polymer.

In certain embodiments, the method further comprises treating the diacid of formula (II) with an acid anhydride (e.g., acetic anhydride), vacuum and heat to provide the corresponding polymer.

In certain embodiments, the diacid of formula (II) is treated with 2 equivalents of acetic anhydride.

In certain embodiments, the diacid of formula (II) is treated with 3 equivalents of acetic anhydride.

In certain embodiments, the method further comprises treating the hydroxy-carboxylic acid compound with a compound of formula (I) in the presence of a base.

In certain embodiments, the base is pyridine, 2,4,6-collidine or poly(4-vinylpyridine).

In certain embodiments, the method further comprises washing the corresponding polymer with water or cyclopentyl methyl ether (CPME).

Certain embodiments of the present invention provide additional processes and intermediates disclosed herein that are useful for preparing PAEs (see, e.g. the Examples).

Leaving Group (Y)

As described herein, each Y is independently a leaving group. In certain embodiments, each Y is independently a leaving group selected from a halogen, alkylsulfonyl or arylsulfonyl leaving group. In certain embodiments, each Y is independently a leaving group selected from chloro, bromo, iodo, mesylate and tosylate.

In certain embodiments, each Y is chloro. Accordingly, in certain embodiments, the compound of formula (I) is a compound of formula (Ia):

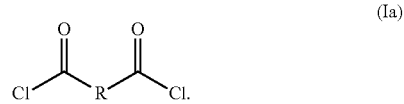

Biologically Active Compounds

The methods of the invention are useful for preparing polymers from biologically active compounds that have at least one carboxylic acid group and one hydroxy group. It should be understood that in formula II, when X is the "residue of a biologically active compound," X represents the structure of the biologically active compound other than the oxy group (—O—) and the carboxy group (—COOH) shown attached to X in formula (II).

Biologically active compounds that may be used in the methods described herein generally have a relatively low molecular weight of approximately 1,000 daltons or less (e.g., about 900 daltons, 800 daltons, 700 daltons, 600 daltons, 500 daltons, 400 daltons, 300 daltons, 200 daltons, 100 daltons, 50 daltons, etc.). Additionally, these compounds must contain within their molecular structure at least one carboxylic acid group and one hydroxy group; however, the hydroxy-carboxylic acid compound can also comprise other functional groups.

The term "biologically active compound" includes therapeutic compounds that provide a therapeutically desirable effect when administered to an animal (e.g., a mammal, such as a human). Therapeutic compounds that can be incorporated into the polymers of the invention include suitably functionalized analgesics, anesthetics, anticancer, anti-Parkinson's agents, anti-infectives, antiacne agents, antibiotics, antioxidants, antimicrobials, anticholinergics, anticoagulants, anticonvulsants, antidiabetic agents, antidyskinetics, antifibrotic agents, antifibrotics, antifungal agents, antiglaucoma agents, anti-inflammatory agents, antineoplastics, antiosteoporotics, antipagetics, antisporatics, antipyretics, antiseptics/disinfectants, antithrombotics, bone resorption inhibitors, calcium regulators, cardioprotective agents, cardiovascular agents, central nervous system stimulants, cholinesterase inhibitors, contraceptives, deodorants, dopamine receptor agonists, erectile dysfunction agents, fertility agents, gastrointestinal agents, gout agents, hormones, hypnotics, immunomodulators, immunosuppressives, keratolytics, migraine agents, motion sickness agents, muscle relaxants, nucleoside analogs, obesity agents, ophthalmic agents, osteoporosis agents, parasympatholytics, parasympathomimetics, prostaglandins, psychotherapeutic agents, respiratory agents, sclerosing agents, sedatives, skin and mucous membrane agents, smoking cessation agents, sympatholytics, synthetic antibacterial agents, ultraviolet screening agents, urinary tract agents, vaginal agents, and vasodilators (see Physicians' Desk Reference, 55 ed., 2001, Medical Economics Company, Inc., Montvale, N.J., pages 201-202).

Suitable examples of low molecular weight drugs with the required functional groups within their structure can be found in almost all classes of drugs including, but not limited to, antioxidants, analgesics, anesthetics, antiacne agents, antibiotics, synthetic antibacterial agents, antimicrobial anticholinergics, anticoagulants, antidyskinetics, antifibrotics, antifungal agents, antiglaucoma agents, anti-inflammatory agents, antineoplastics/anticancer, antiosteoporotics, antipagetics, anti-Parkinson's agents, antisporatics, antipyretics, antiseptics/disinfectants, antithrombotics, bone resorption inhibitors, calcium regulators, keratolytics, sclerosing agents and ultraviolet screening agents. Additional lists of therapeutic compounds can be found, for example, in: Physicians' Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J. One skilled in the art can readily select therapeutic compounds that possess the necessary functional groups for use in the methods described herein from these lists.

In certain embodiments, the biologically active compound is an antioxidant, an antimicrobial, an antifungal, an anticancer, an analgesic, an immunosuppressive or an anti-inflammatory (e.g., a non-steroidal anti-inflammatory).

In certain embodiments, the biologically active compound is an antioxidant. Examples of antioxidants suitable for use in the present invention include, but are not limited to, vanillic acid, syringic acid, coumaric acid, sinapic acid, and ferulic acid.

In certain embodiments, the biologically active compound is an antibacterial compound or an antimicrobial compound. Examples of antibacterial/antimicrobial compounds suitable for use in the present invention include, but are not limited to 4-sulfanilamidosalicylic acid, amoxicillin, apalcillin, aspoxicillin, biapenem, cefadroxil, cefamandole, cefatrizine, cefbuperazone, cefonicid, cefoperazone, cefpiramide, cefprozil, flomoxef, imipenem, meropenem, nadifloxacin, panipenem, salazosulfadimidine, sulfaloxic acid, teicoplanin, and the like.

In certain embodiments, the biologically active compound is an anti-neoplastic or anticancer compound. Examples of anti-neoplastic/anticancer compounds suitable for use in the present invention include, but are not limited to mycophenolic acid, podophyllinic acid 2-ethylhydrazide, ubenimex, and the like.

In certain embodiments, the biologically active compound is an immunosuppressive compound. Examples of immunosuppressive compounds suitable for use in the present invention include, but are not limited to mycophenolic acid, ubenimex and the like.

In certain embodiments, the biologically active compound is an anti-inflammatory compound, such as an NSAID. Examples of anti-inflammatory compounds suitable for use in the present invention include, but are not limited to 3-amino-4-hydroxybutyric acid, fendosal, gentisic acid, mesalamine, olsalazine, oxaceprol, S-adenosylmethionine, sulfasalazinem salicylic acid, diflunisal, salsalate, 5-aminosalicylic acid and the like.

In certain embodiments the anti-inflammatory is salicylic acid.

Linker Molecule (R)

In certain embodiments, each linker molecule (R) is selected from a branched aliphatic, linear aliphatic, and oxygen-containing linker molecule. In certain embodiments, the branched aliphatic, linear aliphatic, or oxygen-containing linker molecule comprises 1 to 15 carbon atoms.

In certain embodiments, R is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—$NR_1$—) or phenylene, and wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, wherein each $R_1$ is independently selected from H or ($C_1$-$C_6$)alkyl.

In certain embodiments, R is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

In certain embodiments, R is a peptide.

In certain embodiments, R is an amino acid.

In certain embodiments, R is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—$NR_1$—) or phenylene, wherein each $R_1$ is independently selected from H or ($C_1$-$C_6$)alkyl.

In certain embodiments, R is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—$NR_1$—) or phenylene, and wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, wherein each $R_1$ is independently selected from H or ($C_1$-$C_6$)alkyl.

In certain embodiments, R is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—$NR_1$—) or phenylene, wherein each $R_1$ is independently selected from H or ($C_1$-$C_6$)alkyl.

In certain embodiments, R is a divalent, branched or unbranched, saturated or unsaturated, hydrocarbon chain, having from 3 to 15 carbon atoms.

In certain embodiments, R is a divalent, branched or unbranched, hydrocarbon chain, having from 3 to 15 carbon atoms.

In certain embodiments, R is a divalent, branched or unbranched, hydrocarbon chain, having from 2 to 10 carbon atoms (e.g., 6 to 10 carbon atoms).

In certain embodiments, R is a divalent hydrocarbon chain having 3, 4, 5, 6, 7, 8, or 9 carbon atoms.

In certain embodiments, R is a divalent hydrocarbon chain having 8 carbon atoms.

In certain embodiments, R is divalent hydrocarbon chain having 4 carbon atoms.

In certain embodiments, R is 1,4 phenylene or 1,3 phenylene.

In certain embodiments R is an adipic linker (—CH$_2$CH$_2$CH$_2$CH$_2$—).

In certain embodiments, R is a diglycolic linker (—CH$_2$OCH$_2$—).

In certain embodiments, R is a diethylmalonic linker (—CH$_2$C(Et)$_2$CH$_2$—).

Average Molecular Weight

In certain embodiments, poly(anhydride-esters) prepared in accordance with the methods of the present invention have an average molecular weight of about 1,000 daltons to about 100,000 daltons. In certain embodiments, the polymer has an average molecular weight of about 5,000 daltons to about 100,000 daltons. In certain embodiments, the polymer has an average molecular weight of about 5,000 daltons to about 50,000 daltons. In certain embodiments, the polymer has an average molecular weight of about 10,000 daltons to about 30,000 daltons. In certain embodiments, the polymer has an average molecular weight greater than about 20,000 daltons and less than about 30,000 daltons.

CERTAIN SPECIFIC EMBODIMENTS

Certain embodiments of the invention provide a method comprising treating salicylic acid with a compound of formula (Ia):

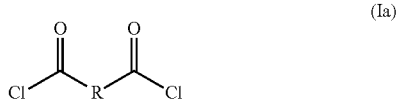

(Ia)

in the absence of a solvent, to provide a diacid of formula (IIa):

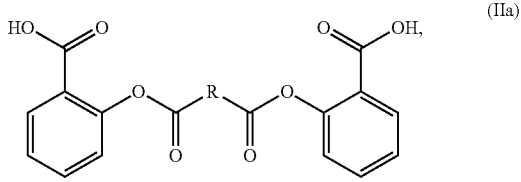

(IIa)

wherein R is a linker molecule.

In certain embodiments, the method further comprises treating the diacid of formula (IIa) with an acid anhydride (e.g., acetic anhydride) and heat to provide the corresponding polymer.

In certain embodiments, the method further comprises treating the diacid of formula (IIa) with an acid anhydride (e.g., acetic anhydride), vacuum and heat to provide the corresponding polymer.

The following non-limiting Examples set forth herein below illustrate certain aspects of the invention.

Example 1

Synthesis of Bioactive Based Poly(anhydride-esters) Via Green Solvent Free Chemistry: One-Pot Polymer Synthesis Abstract SA-based PAEs were synthesized via a one-pot methodology that requires minimal purification and drastically reduces reaction time. For instance, SA-based PAEs were synthesized via solvent free methods by linking two SA moieties with an acyl chloride to form an SA diacid within minutes, which can be activated and subsequently polymerized under high vacuum and heat to form product. Products were then purified using nontoxic and environmentally safe solvents. Polymers and their precursors were then characterized to ensure the greener methodology did not have a detrimental influence on physiochemical and thermal properties. Similar methodologies were explored to synthesize and characterize FA-based PAEs.

PAE Synthesis and Characterization

Figure 2:
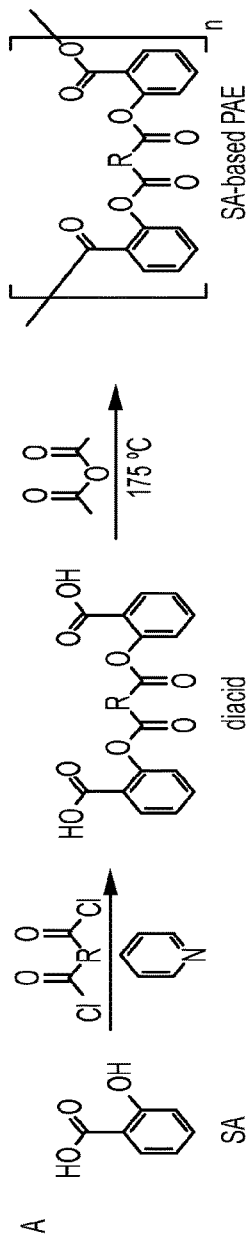
FIG. 2. A. Schemes illustrating one-pot synthesis of SA-PAEs. B. H-NMR of SA-PAE synthesized using one-pot synthesis.
Figure 2:
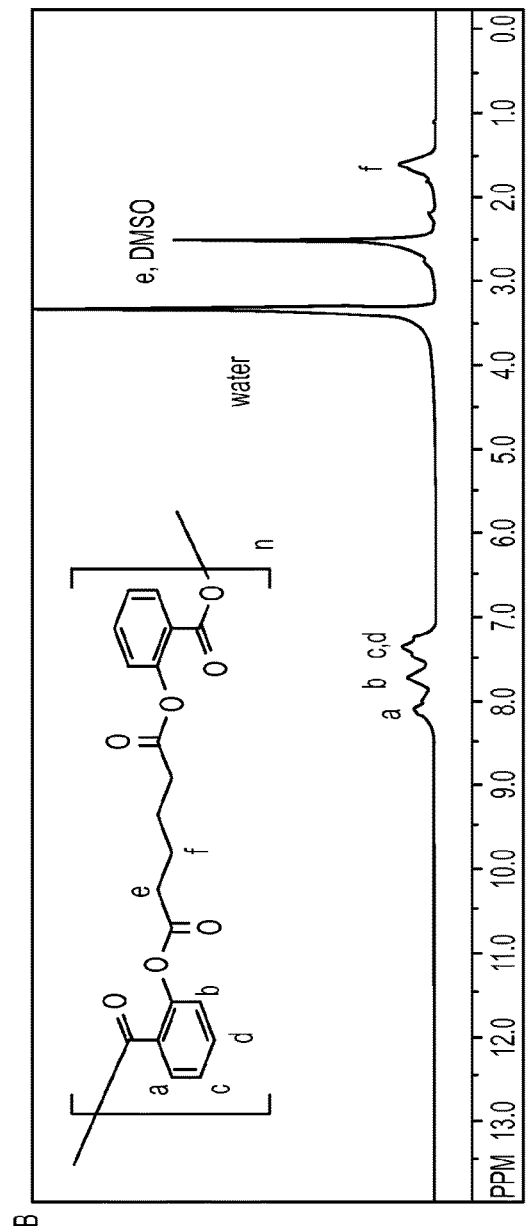

PAEs were synthesized using various green methodologies and characterized (see, FIG. 2A). Specifically, PAEs were characterized via $^1$H Nuclear Magnetic Resonance spectroscopy (FIG. 2B), differential scanning calorimetry, gel permeation chromatography and Fourier transform infrared spectroscopy to elucidate that desired products were synthesized without the presence of impurities.

Solvent Free SA Diacid Synthesis.

Eliminating the use of solvents significantly reduces reaction time, waste and leads to simpler purification. In certain embodiments, the reaction can be carried out using vortexing, which may involve the use of steel balls, or mechanical stirring (e.g., to overcome high viscosity).

TABLE 1

| Synthetic Method | Reaction Time | Yield |
|---|---|---|
| Traditional | 3 hrs | 70% |
| Vortexing | 5 min | 49% |
| Mechanical Stirring | 30 min | 82% |

Purification Methods.

CPME is a safer alternative to acetone and hexanes due to its low toxicity and higher flash point. CPME has very low peroxide forming potential and is a reusable solvent. Water is the most ideal solvent due to its low toxicity, renewability and abundance.

TABLE 2

| Solvent | Amount Needed to Purify 1 gram |
|---|---|
| Acetone/Hexanes | 60 mL/300 mL |
| Cyclopentyl methyl ether (CPME) | 7.5 mL |
| Water | 70 mL |

One Pot Polymer Synthesis.

A one pot polymer synthesis improves synthetic efficiency due to a reduced amount of steps and decreases reaction time significantly. Additionally, synthesis involving the use of solvent can leave solvent trapped in the polymer matrix making it unsuitable for biological purposes. By switching to a one pot solvent free method, it can be ensured that no solvent impurities will be left behind.

Prior to performing one-pot synthesis, salicylic acid (SA) purity (98% purity acceptable) is assessed via $^1$H-NMR spectroscopy. Additionally, anhydrous pyridine, adipoyl chloride, and anhydrous acetic anhydride are confirmed to be colorless liquids. SA (1, 1.00 g, 7.24 mmol) is then dissolved in anhydrous pyridine (1.17 mL, 14.5 mmol) in a 4 dram vial. Upon dissolution, the solution is transferred via syringe to an oven-dried, two-neck 100 mL round-bottom flask (RBF) equipped with a Teflon stirrer, stirrer adaptor, and rubber septum under nitrogen. The mechanical stirrer is set to 120 rpm after which adipoyl chloride (0.58 mL, 4.0 mmol) is added drop-wise manually. Following adipoyl chloride addition, the reaction is allowed to stir an additional 30 minutes. Acetic anhydride (1.71 mL, 18.1 mmol) is then added via syringe and the mixture heated to 75° C. with mechanical stirring (120 rpm). Upon complete dissolution, the reaction is allowed to stir an additional hour, after which the RBF is re-equipped with a vacuum adaptor and pressure reduced below 2 mmHg with continuous stirring. Following removal of excess acetic anhydride, the reaction is heated to 175° C. and stirred until vitrification or constant viscosity (~3-4 h). Once constant viscosity is achieved, the reaction is cooled to room temperature, vacuum removed, and placed under nitrogen. The resulting crude polymer is dissolved in anhydrous DCM (10 mL) and precipitated over 400 mL chilled diethyl ether. Solvent is then decanted and polymer dried under vacuum at room temperature.

TABLE 3

Comparison of traditional and one-pot SA-PAE physicochemical and thermal properties.

| Properties | SA-based PAEs via Traditional Methods | SA-based PAEs via One-Pot Synthesis |
|---|---|---|
| Glass Transition Temperature | 48° C. ± 8.0* | 47° C. ± 7.6§ |
| Overall Percent Yield | 44% | 47% |
| Reaction Time | 48 hrs | <12 hrs |
| Polydispersity Index | 1.5 ± 0.5* | 1.4 ± 0.1§ |
| Molecular Weight | 14.2 ± 6.8 kDa* | 24.7 kDa ± 2.0 kDa§ |

*Averages compiled over a period of time.
§Averages of one pot polymerization

The PAEs described herein may be further characterized by investigating their drug release properties; these experiments may be performed using techniques and assays known in the art, for example [Erdmann, L. et al. *Biomaterials*, 2000, 21, 1941-1946].

Additionally, these methods described herein may be used to synthesize PAEs comprising other hydroxy-carboxylic acid compounds.

Finally, to further improve the green properties of these methods, pyridine could also be replaced in the base catalyzed reaction with other suitable reagents that are less toxic, renewable, and/or increase the synthetic efficiency, such as 2,4,6-collidine or poly(4-vinylpyridine).

Conclusions

Polymers and polymer precursors were successfully synthesized using solvent free methods. SA-based PAEs were synthesized via a one-pot system. Polymer characterization revealed that greener synthetic methodology did not adversely influence thermal and physicochemical properties. Non-toxic purification techniques decreased the amount of solvent required and increased yield. By substituting traditional methods and green syntheses it was possible to increase efficiency and subsequently reduce the environmental impact while creating a safer work environment.

Example 2

Exploring Green Methods Through a One Pot Salicylic Acid-Based Poly(Anhydride-Ester) Synthesis.

Salicylic acid-based poly(anhydride-esters), containing adipic-linkages, were prepared by a one-pot melt-condensation polymerization. One-pot polymer physicochemical and thermal properties were characterized and compared to salicylic acid-based poly(anhydride-esters) produced via traditional synthesis. The one-pot polymerization was found to drastically reduce reaction time while maintaining overall reaction yield. Furthermore, the one-pot polymer produced higher molecular polymer while still possessing similar thermal properties and polydispersity. In addition to increasing efficiency, the one-pot polymer was found to be a greener alternative, improving atom economy, minimizing solvent use and reducing waste.

As described herein, traditional SA-based PAE synthesis has been modified to increase efficiency while reducing raw material consumption and minimizing solvent use. SA Diacid synthesis, from SA and adipoyl chloride, and melt-condensation polymerization were performed sequentially in one-pot to drastically reduce reaction time (Scheme 1). The one-pot SA-based PAE (SA-OP) was characterized by proton ($^1$H) nuclear magnetic resonance (NMR) and Fourier-transform infrared resonance (FTIR) spectroscopies. Polymer weight-averaged $M_w$ and polydispersity index were quantified by gel permeation chromatography (GPC) while thermal properties were evaluated by thermogravimetric analysis (TGA) to obtain decomposition temperature ($T_d$) and differential scanning calorimetry (DSC) to acquire glass transition temperature ($T_g$). Furthermore, SA-OP cytotoxicity tests were conducted to ensure this modified procedure did not adversely impact cytocompatibility.

Scheme 1.

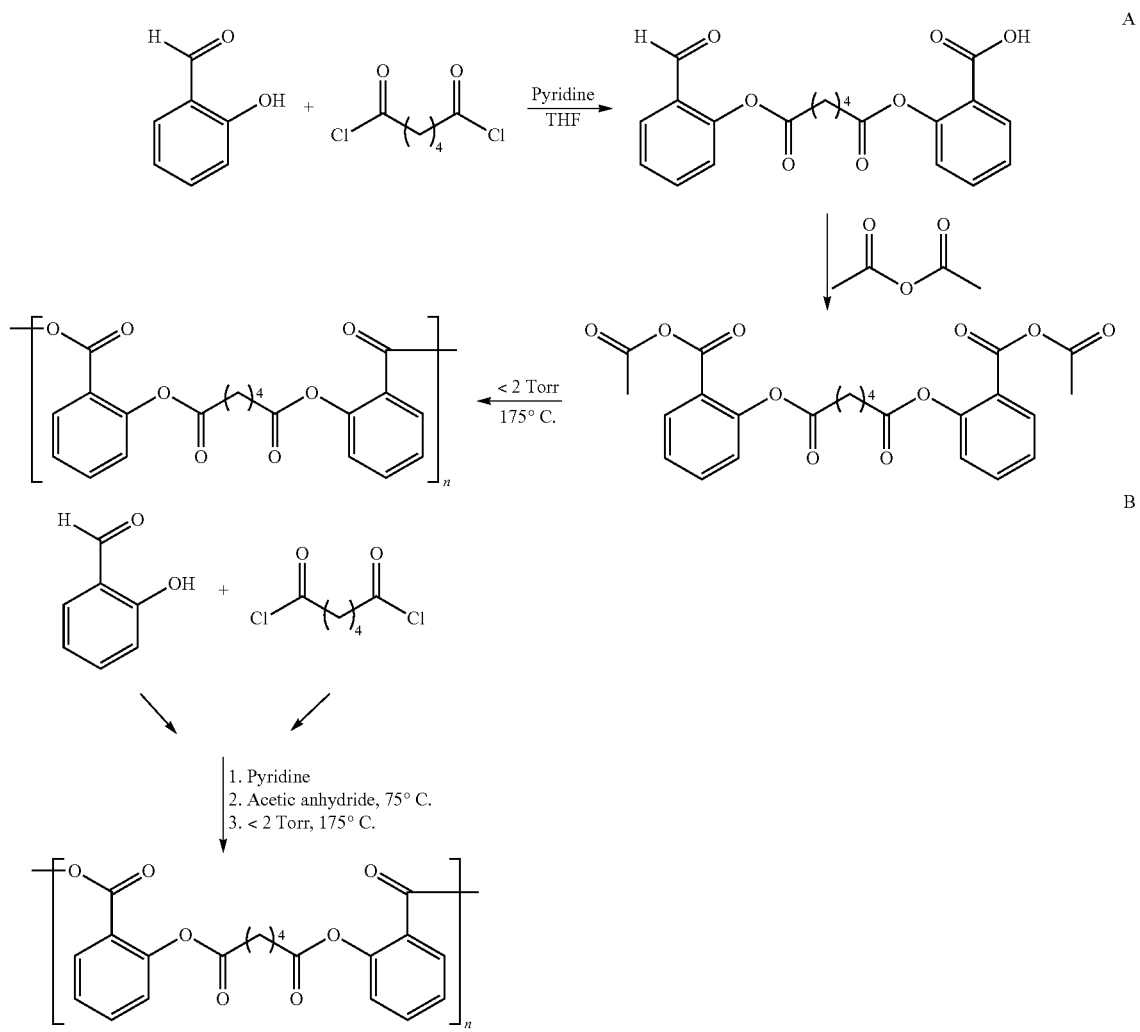

Materials and Methods

Materials.

1 N hydrochloric acid (HCl) and polytetrafluoroethylene (PTFE) syringe filters were purchased from Fisher Scientific (Fair Lawn, N.J.). All other chemicals were acquired from Sigma-Aldrich (Milwaukee, Wis.).

$^1$H NMR and FTIR Spectroscopies.

$^1$H NMR spectroscopy was recorded on a Varian 400 MHz spectrometer by dissolving polymer or polymer precursor samples (~10 mg) in deuterated dimethyl sulfoxide (DMSO-d$_6$), which was also an internal reference. FTIR spectra were obtained using a Nicolet/Avatar 360 spectrophotometer. Spectra were acquired by either grinding and pressing polymer precursors (1 wt. %) with potassium bromide (KBr) into discs or solvent casting polymers, via dichloromethane (DCM), onto sodium chloride (NaCl) plates.

Molecular Weight.

GPC was utilized to determine polymer weight-averaged M$_w$ and PDI. GPC consisted of a Waters (Milford, Mass.) system with a 1515 Isocratic HPLC pump, a 717plus autosampler, and a 2414 refractive index detector. Waters Breeze 3.20 software operating on an IBM ThinkCentre CPU was used for data processing and analysis. Polymers were solved in DCM (10 mg/mL), filtered through 0.45 PTFE syringe filters. Sample aliquots (10 µL) were injected, and resolved, on a Jordi divinylbenzene mixed-bed GPC column (7.8×300 mm, Alltech Associates, Deerfield, Ill.) at 25° C., with DCM as the mobile phase at a flow rate of 1.0 mL/min. Molecular weights were calibrated relative to broad polystyrene standards (Polymer Source Inc., Dorval, Canada).

Thermal Analysis.

TGA was performed to acquire polymer sample decomposition temperature (T$_d$). TGA was conducted using a Perkin Elmer (Waltham, Mass.) TGA7 analyzer with TACT/DX controller equipped with a Dell OptiPlex Gx 110 computer running on Perkin Elmer Pyris software. Polymer samples (~5 mg) were heated under nitrogen at a rate of 10° C./min from 25-400° C. T$_d$ was defined as the onset of decomposition, indicated by the beginning of a sharp slope on the thermogram.

DSC measurements were acquired using a Thermal Advantage (TA; New Castle, Del.) DSC Q200 running on an IBM ThinkCentre computer equipped with TA Universal Analysis software for data acquisition and processing. Polymer glass transition temperature ($T_g$) were procured. Samples (4-6 mg) were heated from −10-200° C. at a rate of 10° C./min with a minimum of two cycles for each sample. The resulting data was analyzed using TA Instruments Universal Analysis 2000 software.

Traditional Polymer Synthesis.

SA (1.00 g, 7.24 mmol) is dissolved in tetrahydrofuran (THF, 10 mL) under inert gas in a 50 mL round-bottomed flask (RBF). Pyridine (14.5 mmol) is added via syringe and the reaction magnetically stirred for 15 min at room temperature (RT). Adipoyl chloride (2, 3.80 mmol) is added dropwise to the reaction solution over 1 hr. After stirring an additional 2 hrs at RT, the reaction mixture is quenched over 70 mL Deionized (DI) $H_2O$ and acidified to ~pH=2, using concentrated HCl, in a 250 mL beaker. Crude diacid is isolated via vacuum filtration, washed 3×20 mL DI $H_2O$, and allowed to air dry. Crude diacid is then dissolved in acetone (60 mL) with heating (40° C.) and reprecipitated in 5-fold excess hexanes with continued stirring and cooling to RT. Product is then isolated via vacuum filtration and dried in vacuum oven at 60° C. for >12 hrs.

SA (Adipic) Diacid.

Yield: 71.5% (performed in triplicate, white powder). $^1$H NMR (400 MHz, DMSO-$d_6$): δ 7.95 (d, 2H, ArH), 7.65 (t, 2H, ArH), 7.40 (t, 2H, ArH), 7.20 (d, 2H, ArH), 2.65 (t, 4H, CH2), 1.75 (m, 4H, CH2). FTIR (KBr, cm$^1$): 1727 (C=O, ester), 1690 (C=O, acid).

SA Diacid (3, 0.97 g) is stirred in excess acetic anhydride (~10 mL) at RT under inert gas in 50 mL RBF until suspension becomes a clear solution (6-12 hrs). Excess acetic anhydride is removed in vacuo to acquire activated monomer (4). Monomer (4, 2.52 mmol) is placed under vacuum (>2 Torr) and brought to 175° C. with active stirring (Teflon stirrer) at 120 rpm with overhead stirrer. Reaction proceeds until vitrification or polymer viscosity is attained (~3 hrs). Upon completion, reaction is cooled to RT, dissolved in 10 mL DCM, and precipitated in 400 mL chilled diethyl ether. Resulting polymer is isolated via decantation or vacuum filtration and dried under vacuum (>12 hrs, RT).

SA (Adipic) PAE.

Yield: 61.8% (tan powder). $^1$H NMR (400 MHz, DMSO-$d_6$): δ 8.15 (b, 2H, ArH), 7.75 (b, 2H, ArH), 7.40 (b, 4H, ArH), 2.60 (b, 4H, CH2), 1.60 (b, 4H, CH2). FTIR (NaCl, cm$^{-1}$): 1781, 1705 (C=O, anhydride), 1734 (C=O, ester).

One-Pot Polymer Synthesis.

SA (1, 1.00 g, 7.24 mmol) is dissolved in anhydrous pyridine (1.17 mL, 14.5 mmol) in a 20 mL scintillation vial. Upon dissolution, the solution is transferred via syringe to an oven-dried, two-neck 100 mL RBF equipped with a Teflon stirrer, stirrer adaptor, and rubber septum under nitrogen. The mechanical stirrer is set to 120 rpm after which adipoyl chloride (0.58 mL, 3.98 mmol) is added drop-wise manually. Following adipoyl chloride addition, the reaction is allowed to stir an additional 30 minutes after which acetic anhydride (1.71 mL, 1.8.1 mmol) is added via syringe and mixture heated to 75° C. After complete dissolution, the RBF is equipped with a vacuum adaptor and pressure reduced below 2 mmHg with continuous stirring. Once excess acetic anhydride is completely removed, the reaction is heated to 175° C. and stirred until vitrification or constant viscosity (~3-4 h). Once achieved, the reaction is cooled to room temperature, vacuum removed, and placed under nitrogen. The crude polymer is dissolved in anhydrous DCM (10 mL) and precipitated over 400 mL chilled diethyl ether. Solvent is then decanted and polymer (4) dried under vacuum at room temperature. Polymer properties are presented in Table 4. Yield: 47.4% (tan powder). $^1$H NMR (400 MHz, DMSO-$d_6$): δ 8.15 (b, 2H, ArH), 7.75 (b, 2H, ArH), 7.40 (b, 4H, ArH), 2.60 (b, 4H, CH2), 1.60 (b, 4H, CH2). FTIR (NaCl, cm$^{-1}$): 1780-1710 (C=O ester and anhydride)

Cytotoxicity Studies.

In vitro cytotoxicity studies were conducted by culturing 3T3 mouse fibroblasts in cell media (Dulbecco's Modified Eagle Medium supplemented with 10% Fetal Bovine Serum, 1% Penicillin Streptomycin) containing SA (adipic) PAEs from traditional (SA-traditional) and SA-OP synthesis. Polymers were sterilized under UV at λ=254 nm for 900 s (Spectronics Corporation, Westbury, N.Y.) prior to being dissolved in DMSO and subsequently diluted with cell media to reach concentrations of 0.1 mg/mL, 0.01 mg/mL and 0.001 mg/mL. Aliquots of cell media containing polymers were then distributed to allocated wells in a 96-well plate with 2000 cells/well and incubated at 37° C. DMSO-containing cell media (1%) was used as a negative control.

Cell viability was determined using CellTiter 96® Aqueous One Solution Cell Proliferation Assay. After 24 h, 48 h, and 72 h incubation with polymers, 20 μL of (3-(4,5-dimethylthiazol-2-yl)-5-(3-carboxymethoxyphenyl)-2-(4-sulfophenyl)-2H-tetrazolium) (MTS) reagent was added to each well and further incubated for 4 h at 37° C. Absorbance was then recorded with a microplate reader (Coulter, Boulevard Brea, Calif.) at 492 nm.

Results and Discussion

Traditionally SA-based PAEs were synthesized via a two-step reaction pathway in which SA is first reacted with a diacyl chloride in THF with pyridine to facilitate SA Diacid synthesis (Schmeltzer R. C. ATJ, Uhrich K. E. Optimized Synthesis of Salicylate-based Poly(anhydride-esters). Polym Bull. 2003; 49:441-8). Pyridine deprotonates SA's carboxylic acid and subsequently catalyzes O-acylation through an acyl-pyridinium ion. Though yields were near quantitative further purification was often necessary to acquire other SA Diacids (i.e., SA adipic Diacid). This was usually achieved through an acetone/hexanes reprecipitation in which crude SA Diacid is first dissolved in acetone and then precipitated using five times the volume of hexanes. Additionally, prolonged vacuum drying with heat was frequently necessary to completely remove THF. In the absence of excessive drying, solvent would often persist after polymerization as indicated by $^1$H NMR. Following SA Diacid acquisition, acetic anhydride is used to activate the carboxylic acid functionalities. After activation excess acetic anhydride (~80 eq) would need to be removed in vacuo and the resulting monomer transferred prior to melt-condensation polymerization. These additional steps introduce opportunities in which the activated carboxylic acids could be hydrolyzed and subsequently result in a lower $M_w$ polymer.

SA-OP was synthesized via a similar two-step synthetic method in a one-pot reaction. The near quantitative O-acylation of SA with adipoyl chloride was carried out in stoichiometric amounts of pyridine to generate SA (adipic) Diacid as a white paste. Diacid was then activated with acetic anhydride at 75° C. prior to being placed under vacuum (>2 Torr) and heated to 175° C. to acquire SA-OP. The one-pot method was conducted in triplicate to confirm reproducibility and its polymer properties and reaction efficiency compared to SA-traditional.

TABLE 4

Polymer properties and reaction efficiency of SA-OP vs SA-traditional.

| Properties | SA adipic PAE via traditional method | SA adipic PAE via one-pot method |
|---|---|---|
| $T_g$ | 48° C. ± 8.0* | 47° C. ± 7.6‡ |
| $M_w$ | 14.2 ± 6.8 kDa* | 24.7 ± 2.0 kDa‡ |
| PDI | 1.5 ± 0.5* | 1.4 ± 0.1‡ |
| Overall Percent Yield | 44% | 47% |
| Reaction Time | 24-30 h | <12 h |

*denotes averages compiled over 12 years whereas ‡denotes averages of SA-OP in triplicate.

SA-OP exhibited comparable overall reaction yield while drastically decreasing the amount of time necessary to produce SA adipic PAE from SA (Table 4). Contributing to the enhanced reaction efficiency was the elimination of solvents during the synthesis (THF) and purification (acetone, hexanes) of SA adipic diacid intermediate. Reduced equivalents of acetic anhydride and removal of activated monomer isolation also improved efficiency. SA-OP displayed higher $M_w$ than SA-traditional, which is likely attributed to the reduced exposure of the monomer with air, as well as similar $T_g$ and PDI values.

Figure 3:
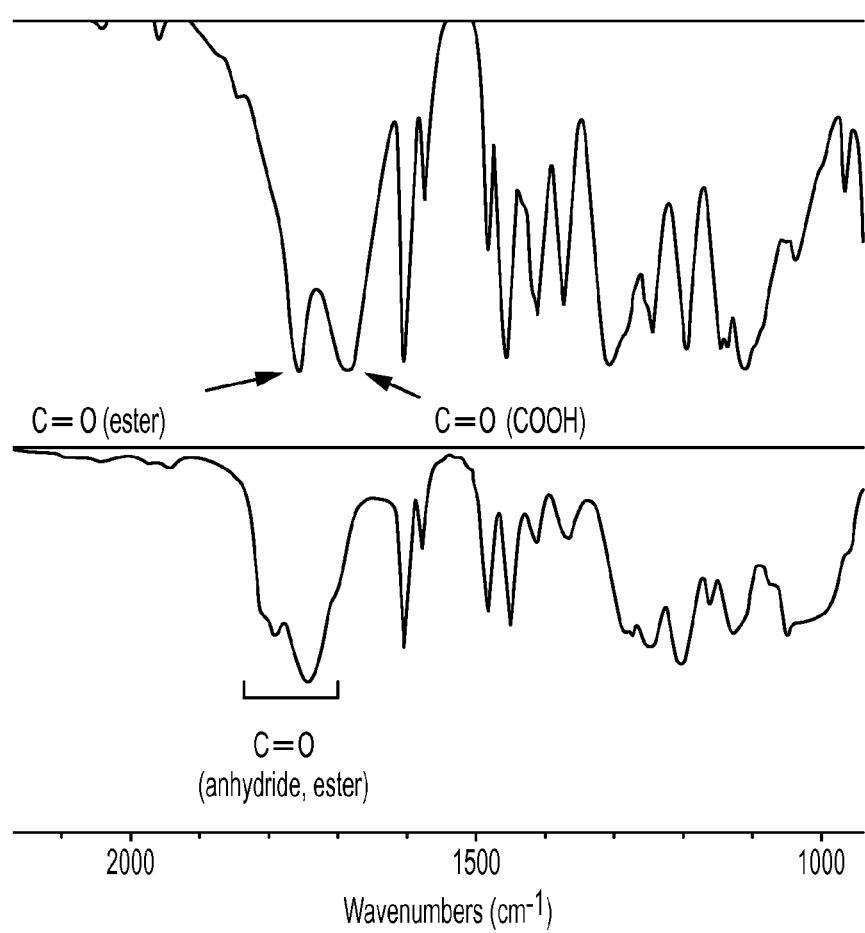
FIG. 3. FTIR Top: SA (adipic) Diacid with C=O ester (1727 cm$^{-1}$) and acid (1690 cm$^{-1}$) via traditional synthesis. Bottom: SA (adipic) PAE C=O anhydride and ester (1780-1710 cm$^{-1}$) via one-pot method.
Figure 4:
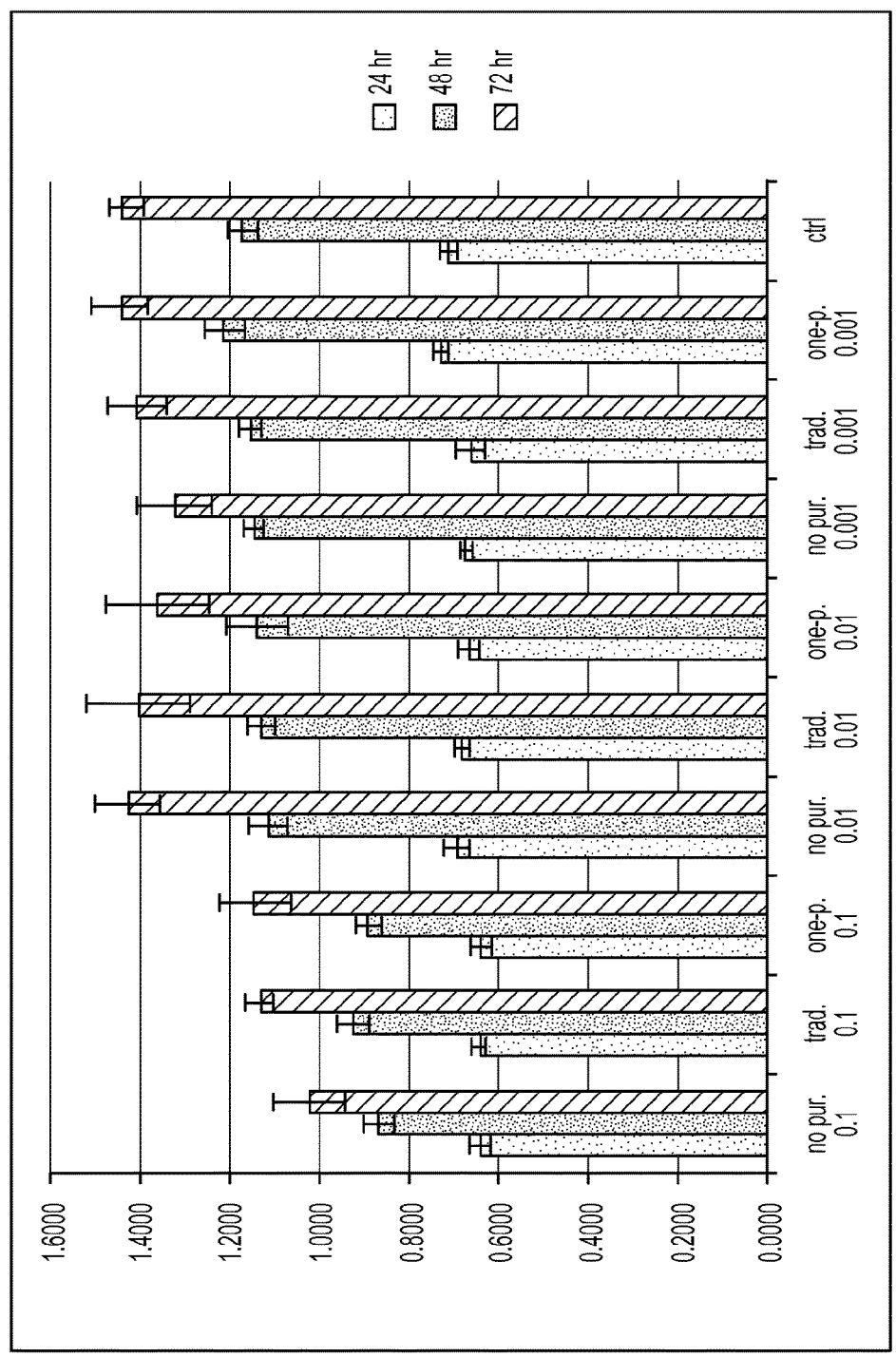
FIG. 4. SA-traditional, SA-OP, and modified SA-OP cytocompatibility in cell culture media at 0.1, 0.01, and 0.001 mg/mL after 24, 48, and 72 h (for each group, the bar representing 24 h is on the left, the bar representing 48 h is in the middle and the bar representing 72 h is on the right).

During SA-OP it is possible that SA adipic diacid synthesis will not be quantitative and side-products (SA, adipic acid, mono-conjugated SA) may persist in small quantities. While pure monomer is desirable prior to polymerization, the side-products are all degradation products of SA adipic PAE. As SA-OP polymer is pure by $^1$H NMR and FTIR spectroscopies (FIG. 3), it is hypothesized that any side-products present prior to activation are either incorporated in the polymer anhydride-ester network or removed by fractionation following the polymerization. An additional concern was pyridine and pyridine HCl removal following SA O-acylation. Pyridine and pyridine HCl boil at 115 and 222-224° C. respectively, and thus can be removed by the high temperature and low pressure of the polymerization process. Nonetheless, cytotoxicity studies (FIG. 4) were conducted comparing SA-traditional, SA-OP, and a modified SA-OP in which pyridine is removed prior to activation using an acidic wash. All polymers were shown to be cytocompatible at 0.01 mg/mL and lower concentrations after 72 h. It is important to note that SA-traditional, SA-OP, and modified SA-OP did not display statistically different cytotoxicity at any concentration or time point. Thus, it can be concluded that SA-OP does not contain sufficient levels of pyridine or pyridine HCl to be detrimental to its cytocompatibility profile.

Conclusion

SA adipic PAEs were successfully synthesized using a one-pot melt-condensation polymerization method. SA-OP was found to be a more efficient synthetic method, drastically reducing reaction time while increasing weight-averaged $M_w$ and maintaining thermal properties. Additionally, cytotoxicity studies revealed that SA adipic PAEs synthesized via the SA-OP methodology displayed no statistical difference from PAEs synthesized via the traditional method. Furthermore, similar polymerization yields were obtained for both methods following purification. Thus, this one-pot polymerization method offers a greener, more effective means of producing SA adipic PAEs, saving environmental and raw material costs.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:

1. A method comprising treating a hydroxy-carboxylic acid compound:

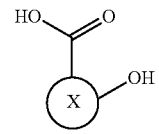

with a compound of formula (I):

(I)

in the presence of a base and in the absence of a solvent, to provide a diacid of formula (II):

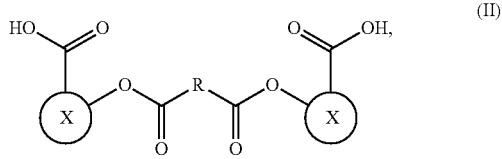

(II)

wherein R is a linker molecule; wherein each Y is independently a leaving group; and wherein X is a residue of a biologically active compound.

2. The method of claim 1, further comprising treating the diacid of formula (II) with acid anhydride, heat and vacuum to provide the corresponding polymer.

3. The method of claim 1, wherein the biologically active compound is an antioxidant, an antimicrobial, an antifungal, an anticancer, an analgesic, an immunosuppressive or an anti-inflammatory.

4. The method of claim 3, wherein the biologically active compound is an anti-inflammatory compound.

5. The method of claim 4, wherein the anti-inflammatory compound is salicylic acid.

6. The method of claim 3, wherein the biologically active compound is an antioxidant.

7. The method of claim 1, wherein the base is pyridine, 2,4,6-collidine or poly(4-vinylpyridine).

8. The method of claim 1, wherein R is a branched aliphatic, linear aliphatic or oxygen-containing linker molecule.

9. The method of claim 1, wherein R is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—NR$_1$—) or phenylene, and wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, and wherein each $R_1$ is independently selected from H or ($C_1$-$C_6$)alkyl.

10. The method of claim 1, wherein R is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

11. The method of claim 1, wherein R is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—NR$_1$—) or phenylene, and wherein each $R_1$ is independently selected from H or ($C_1$-$C_6$)alkyl.

12. The method of claim 1, wherein R is a divalent, branched or unbranched, hydrocarbon chain, having from 3 to 15 carbon atoms.

13. The method of claim 12, wherein R is a divalent hydrocarbon chain having 2 to 10 carbon atoms.

14. The method of claim 13, wherein R is —CH$_2$CH$_2$CH$_2$CH$_2$—.

15. The method of claim 1, wherein each Y is independently a leaving group selected from a halogen, alkylsulfonyl or arylsulfonyl leaving group.

16. The method of claim 1, wherein each Y is independently a leaving group selected from chloro, bromo, iodo, mesylate and tosylate.

17. The method of claim 1, wherein the compound of formula (I) is a compound of formula (Ia):

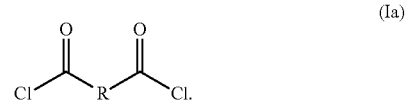

(Ia)

18. The method of claim 2, wherein the polymer has an average molecular weight of about 10,000 daltons to about 30,000 daltons.

19. The method of claim 2, wherein the polymer has an average molecular weight greater than about 20,000 daltons and less than about 30,000 daltons.

20. The method of claim 1, wherein the base is pyridine.

* * * * *